US00PP23038P2

(12) United States Plant Patent
Hooijman

(10) Patent No.: US PP23,038 P2
(45) Date of Patent: Sep. 18, 2012

(54) ROSE PLANT NAMED 'ESM NACAR'

(50) Latin Name: *Rosa hybrida*
Varietal Denomination: Esm Nacar

(75) Inventor: Aloysius A. J. Hooijman, Aalsmeer (NL)

(73) Assignee: Esmeralda Breeding B.V., Aalsmeer (NL)

( * ) Notice: Subject to any disclaimer, the term of this patent is extended or adjusted under 35 U.S.C. 154(b) by 0 days.

(21) Appl. No.: 13/134,375

(22) Filed: Jun. 6, 2011

(51) Int. Cl.
*A01H 5/00* (2006.01)

(52) U.S. Cl. ..... Plt./133

(58) Field of Classification Search ..... Plt./133
See application file for complete search history.

*Primary Examiner* — Kent L Bell
(74) *Attorney, Agent, or Firm* — C. A. Whealy

(57) ABSTRACT

A new and distinct cultivar of Rose plant named 'Esm Nacar', characterized by its upright and moderately strong flowering stems; moderately vigorous growth habit and high productivity; early flowering habit; large creamy white-colored flowers that are typically grown as single stems; and excellent post-production longevity.

1 Drawing Sheet

Botanical designation: *Rosa hybrida.*
Cultivar denomination: 'ESM NACAR'.

BACKGROUND OF THE INVENTION

The present Invention relates to a new and distinct cultivar of Rose plant, botanically known as *Rosa hybrida*, commercially used as a cut flower Rose plant, and hereinafter referred to by the name 'Esm Nacar'.

The new Rose plant is a product of a planned breeding program conducted by the Inventor in El Quinche, Pichincha, Ecuador. The objective of the breeding program was to develop new freely-flowering cut flower Rose varieties with novel and attractive flower colors and excellent postproduction longevity.

The new Rose plant originated from a cross-pollination made by the Inventor in February, 2002 of a proprietary Rose selection identified as code name Line 5, not patented, as the female, or seed, parent with a proprietary Rose selection identified as code name Line 30, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in January, 2003.

Asexual reproduction of the new Rose plant by cuttings at El Quinche, Pichincha, Ecuador since October, 2003, has shown that the unique features of this new Rose plant are stable and reproduced true to type in successive generations of asexual reproduction.

SUMMARY OF THE INVENTION

Plants of the new Rose have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Esm Nacar'. These characteristics in combination distinguish 'Esm Nacar' as a new and distinct Rose plant:

1. Upright and moderately strong flowering stems.
2. Moderately vigorous growth habit and high productivity.
3. Early flowering habit.
4. Large creamy white-colored flowers that are typically grown as single stems.
5. Excellent postproduction longevity.

Plants of the new Rose differ from plants of the female parent selection in the following characteristics:

1. Plants of the new Rose are taller than plants of the female parent selection.
2. Flowering stems of plants of the new Rose have fewer thorns than flowering stems of plants of the female parent selection.
3. Plants of the new Rose have larger flowers than plants of the female parent selection.
4. Plants of the new Rose and the female parent selection differ in flower color as plants of the female parent selection have white-colored flowers.
5. Flowers of plants of the new Rose open more fully than flowers of plants of the female parent selection.

Plants of the new Rose differ from plants of the male parent selection in the following characteristics:

1. Plants of the new Rose are taller than plants of male parent selection.
2. Plants of the new Rose have smaller flowers than plants of the male parent selection.
3. Plants of the new Rose and the male parent selection differ in flower color as plants of the male parent selection have light pink-colored flowers.

Plants of the new Rose can be compared to plants of Rose 'Tibet', not patented. In side-by-side comparisons conducted in El Quinche, Pichincha, Ecuador, plants of the new Rose differed from plants of 'Tibet' in the following characteristics:

1. Plants of the new Rose were shorter than plants of 'Tibet'.
2. Plants of the new Rose were not as vigorous as plants of 'Tibet'.
3. Plants of the new Rose flowered twelve days earlier than plants of 'Tibet'.
4. Flowers of plants of the new Rose had more petals than flowers of plants of 'Tibet'.

5. Flowers of plants of the new Rose had longer sepals than flowers of plants of 'Tibet'.
6. Plants of the new Rose had creamy white-colored flowers whereas plants of 'Tibet' had white-colored flowers.
7. Flowers of plants of the new Rose were longer lasting than flowers of plants of 'Tibet'.

BRIEF DESCRIPTION OF THE PHOTOGRAPHS

The accompanying colored photographs illustrate the overall appearance of the new Rose plant showing the colors as true as it is reasonably possible to obtain in colored reproductions of this type. Colors in the photographs may differ slightly from the color values cited in the detailed botanical description which accurately describe the colors of the new Rose plant.

The photograph at the upper left of the sheet comprises a side perspective view of a typical flowering stem of 'Esm Nacar'.

The photograph at the upper right of the sheet is a close-up view of a typical flower of 'Esm Nacar'.

The photograph at the bottom left of the sheet is a close-up view of a typical flower of 'Esm Nacar'.

The photographs at the bottom right of the sheet are close-up views of the upper and lower surfaces of typical leaves of 'Esm Nacar'.

DETAILED BOTANICAL DESCRIPTION

Plants of the new Rose have not been observed under all possible environmental conditions and cultural practices. The phenotype may vary somewhat with variations in environment conditions such as temperature and light intensity, without, however, any variance in genotype. The aforementioned photographs, following observations and measurements describe plants grown in 10-liter containers in a polyethylene-covered greenhouse in El Quinche, Pichincha, Ecuador and under typical hydroponic Rose production practices. Plants were pinched about 13 to 14 weeks after planting. Plants were 1.5 years old when the photographs and description were taken. During the production of the plants, day temperatures ranged from 16° C. to 30° C., night temperatures ranged from 12° C. to 16° C. and light levels ranged from 800 to 1,200 foot-candles. In the following description, color references are made to The Royal Horticultural Society Colour Chart, 2001 Edition, except where general terms of ordinary dictionary significance are used.

Botanical classification: *Rosa hybrida* 'Esm Nacar'.

Parentage:

*Female, or seed, parent*.—Proprietary seedling selection of *Rosa hybrida* identified as code name Line 5, not patented.

*Male, or pollen, parent*.—Proprietary seedling selection of *Rosa hybrida* identified as code name Line 30, not patented.

Propagation:

*Type*.—By cuttings.

*Time to initiate roots*.—About seven to ten days at 26° C. to 30° C.

*Time to produce a rooted young plant*.—About four to five weeks at 22° C. to 26° C.

*Root description*.—Fibrous, fine; close to N199B in color.

*Rooting habit*.—Moderately freely branching; medium density.

Plant description:

*Plant form*.—Upright plant habit; upright and moderately strong flowering stems.

*Growth habit*.—Moderately vigorous; freely basal branching habit; dense and bushy growth habit; highly productive with about 14.4 flowering stems developing per plant per year.

*Plant height*.—About 115 cm.

*Plant width* (*spread*).—About 64 cm.

*Lateral branches* (*peduncles*).—Length: About 80 cm. Diameter: About 6.3 mm. Internode length: About 4.9 cm. Texture: Smooth, glabrous. Color: Close to 146A; with development, color becoming closer to N199A. Thorns: Density: Medium density. Shape: Triangular with sharp acuminate apices; slightly incurved. Height: About 7.7 mm. Length, at base: About 8.6 mm. Color, immature: Close to 183B. Color, mature: Close to 178B.

Foliage description:

*Arrangement*.—Alternate; compound with typically seven leaflets per leaf.

*Leaf length*.—About 16.7 cm.

*Leaf width*.—About 12.9 cm.

*Terminal leaflet length*.—About 7.4 cm.

*Terminal leaflet width*.—About 4.6 cm.

*Lateral leaflet length*.—About 5.8 cm.

*Lateral leaflet width*.—About 3.8 cm.

*Leaflet shape*.—Oval.

*Leaflet apex*.—Acute.

*Leaflet base*.—Attenuate.

*Leaflet margin*.—Serrate.

*Leaflet texture, upper surface*.—Smooth, glabrous; coriaceous.

*Leaflet texture, lower surface*.—Prickles along leaf axis.

*Leaflet venation pattern*.—Pinnate.

*Leaflet color*.—Developing leaflets, upper surface: Close to 137A. Developing leaflets, lower surface: Close to 146B. Fully expanded leaflets, upper surface: Between 139A and 147A; venation, close to 146C. Fully expanded leaflets, lower surface: Close to 147B; venation, close to 146D.

*Petioles, leaves*.—Length: About 1.3 cm. Diameter: About 1.9 mm. Texture, upper and lower surfaces: With prickles. Color, upper surface: Close to N199B. Color, lower surface: Close to 146A.

*Petioles, leaflets*.—Length: About 2.1 cm. Diameter: About 1.3 mm. Texture, upper and lower surfaces: With prickles. Color, upper surface: Close to 147A. Color, lower surface: Close to 146B.

*Stipules*.—Arrangement and appearance: Two, adnate to the petiole, leafy in appearance. Length: About 2.2 cm. Width: About 1 mm. Shape: Roughly deltoid. Apex: Acuminate. Base: Truncate. Margin: Serrate, irregular. Texture, upper and lower surfaces: Smooth, glabrous; membranous; pubescence along the margins. Venation pattern: Pinnate. Color, upper surface: Close to 137A. Color, lower surface: Close to 143A.

Flower description:

*Flower type and flowering habit*.—Symmetrical rosette flowers; flowers typically grown as single stems; flowers face upright.

*Flowering season*.—Year-round under greenhouse conditions; early flowering habit, plants begin flowering about 63 days after pinching; in the garden, optimal flowering from spring through autumn; flowering intermittent.

*Flower diameter*.—About 11 cm.

*Flower depth* (*height*).—About 6 cm.

*Flower longevity on plant*.—About 26 days; flowers persistent.

*Flower longevity as a cut flower*.—Excellent postproduction longevity, flowers last about twelve days.

*Fragrance*.—Very faintly fragrant, pleasant.

*Flower buds*.—Shape: Ovoid. Length: About 6 cm. Diameter: About 4 cm. Color: Close to 144A.

*Petals*.—Quantity: About 35 to 40 per flower; petals imbricate. Length: About 6.4 cm. Width: About 6.7 cm. Shape: Nearly round; transversely ovate. Apex: Blunt to shortly acute. Base: Obtuse. Margin: Entire. Texture, upper and lower surfaces: Smooth, glabrous; papery to coriaceous. Color: When opening, upper surface: Between 157A and 150D; towards the base, close to 1C. When opening, lower surface: Close to 150D; towards the base, close to 150C. Fully opened, upper surface: Close to 157C; towards the base, close to 7C. Fully opened, lower surface: Close to 157D; towards the base, close to 8C.

*Sepals*.—Quantity per flower: Typically five. Length: About 5.1 cm. Width: About 1.4 cm. Shape: Roughly deltoid. Apex: Tapered. Base: Truncate. Margin: Entire; ciliate and/or glandular. Texture, upper and lower surfaces: Coriaceous; pubescence along the margins. Color: When opening, upper surface: Between 144C and 147B. When opening, lower surface: Betweem 144A and 146B. Fully opened, upper surface: Between 146D and 146A. Fully opened, lower surface: Between 144A and 146B.

*Reproductive organs*.—Stamens: Quantity: About 92 per flower. Anther length: About 3.7 mm. Anther shape: Reniform. Anther color: Between 161B and N163C. Filament color: Close to 14B. Pollen amount: Moderate. Pollen color: Close to 167A. Pistils: Quantity: About 194 per flower. Pistil length: About 1.7 cm. Stigma shape: Broadly reniform. Stigma color: Close to 161A. Style length: About 1.2 cm. Style color: Close to 155A tinted with close to 45C. Receptacle height: About 1.1 cm. Receptacle diameter: About 9 mm. Receptacle shape: Cup-shaped. Receptacle texture: Smooth, glabrous. Receptacle color: Close to 144A. Fruits/seeds: Fruit and seed development have not been observed on plants of the new Rose.

Pathogen/pest resistance: Plants of the new Rose have not been observed to be resistant to pathogens and pests common to Rose plants.

Temperature tolerance: Plants of the new Rose have been observed to tolerate temperatures ranging from 0° C. to 35° C.

It is claimed:

1. A new and distinct Rose plant named 'Esm Nacar' as illustrated and described.

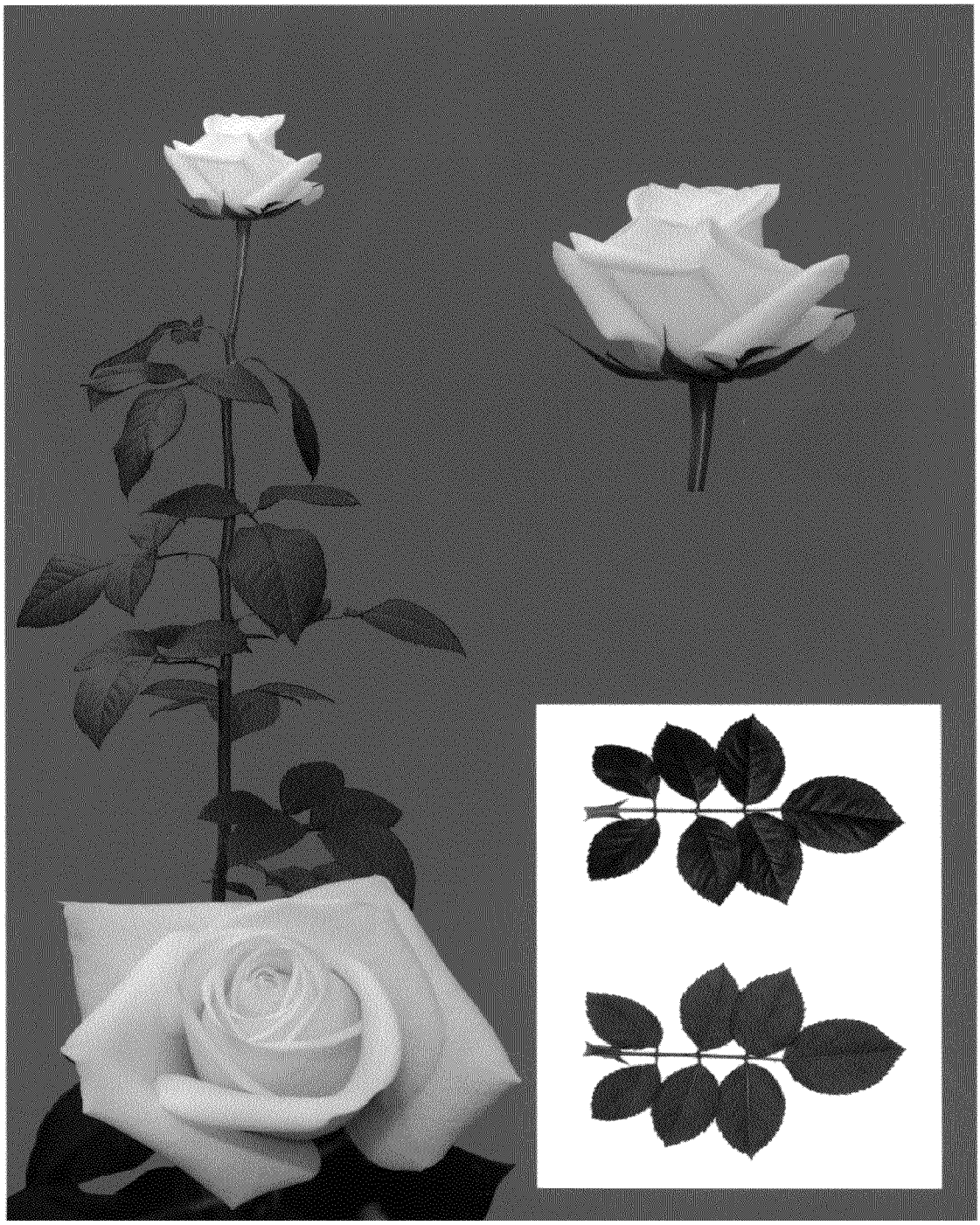

* * * * *